United States Patent [19]

Sherlock

[11] Patent Number: 4,622,981

[45] Date of Patent: Nov. 18, 1986

[54] DRAINAGE BAG SPACER AND BAG INCORPORATING SAME

[75] Inventor: Paul Sherlock, San Francisco, Calif.

[73] Assignee: Sherwood Medical Company, St. Louis, Mo.

[21] Appl. No.: 637,678

[22] Filed: Aug. 3, 1984

[51] Int. Cl.[4] .......................... A61B 5/00; B65D 81/00
[52] U.S. Cl. .................................... 128/762; 128/767; 128/771; 604/322
[58] Field of Search ............... 128/760, 766, 767, 771, 128/DIG. 24, 762; 604/322–326, 332–345; 383/33, 35, 38; 206/45.33, 45.34

[56] References Cited

U.S. PATENT DOCUMENTS 3,902,496  9/1975  Eakin ..................... 604/334
4,178,934 12/1979  Forman ................... 128/295

Primary Examiner—C. Fred Rosenbaum
Assistant Examiner—J. L. Kruter
Attorney, Agent, or Firm—Stanley N. Garber; Andrew J. Beck; William R. O'Meara

[57] ABSTRACT

A spacer is disposed between the flexible front and rear panels of a urinary drainage bag, which bag has an inlet in fluid communication with the outlet of a relatively rigid urine meter. The spacer has ribs which extend out perpendicularly from its body to hold the front and rear panels of the drainage bag apart when urine is dumped from the meter into the bag.

9 Claims, 8 Drawing Figures

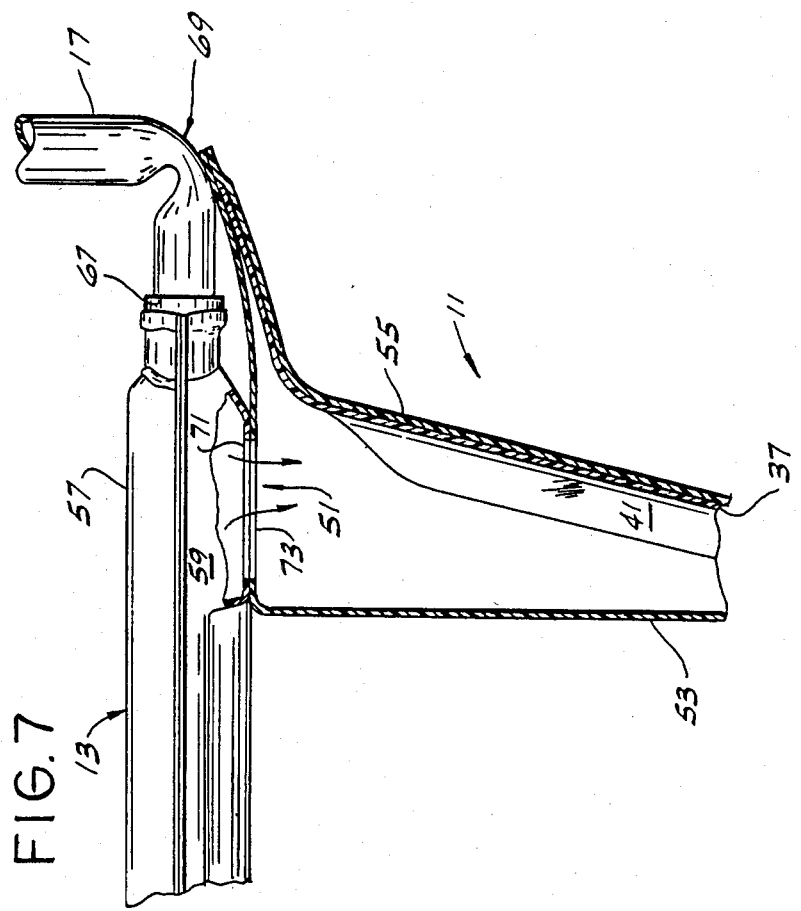
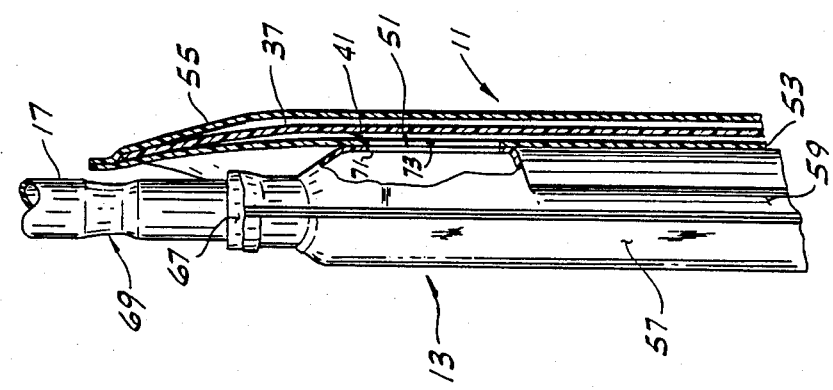

DRAINAGE BAG SPACER AND BAG INCORPORATING SAME

BACKGROUND OF THE INVENTION

This invention relates to urological apparatus and more specifically to urine meter drainage bags.

Drainage bags with a lift type dumping meter such as that shown in U.S. Pat. No. 4,178,934 can manifest meter dumping difficulties if the bag is completely empty or drained and its walls are relatively flat. The proximity of the walls makes it difficult for air to enter from the bag vent rapidly enough to allow the bag to open with sufficient rapidity so as not to impede the dumping rate.

SUMMARY OF THE INVENTION

It is therefore an object of the present invention to promote rapid dumping of urine meters into their associated drainage bags, to separate the panels of the drainage bag without unduly increasing the thickness of the bag, and to achieve these objects in an economical manner. Other features and objects will become apparent as one considers the detailed description of the invention.

In brief, the spacer of the present invention may be used in combination with a drainage bag and a rigid metering collection chamber. The bag has a flexible front panel constituting the front of the bag, a flexible rear panel constituting the rear of the bag, and an inlet port generally near to but spaced from the top of the bag to permit the flow of body fluids into the bag. The flexible front and rear panels of the bag are secured together along their peripheries to form the bag. The rigid metering collection chamber has an inlet port generally near the top thereof for connection to a drain tube or the like to receive body fluids from a patient to be measured. The chamber also has an outlet port generally near the top thereof in fluid communication with the inlet port of the drainage bag to permit body fluids from the metering collection chamber to be manually dumped therefrom into the drainage bag when the collection chamber is lifted from a generally vertical to a generally horizontal position. The spacer is positioned inside the bag between the front and rear panels. It has a relatively flat main body and at least two ribs extending generally perpendicularly out from the body and spaced from each other. The ribs extend at their upper ends to the vicinity of the inlet port of the bag to facilitate the entry of body fluids being dumped therein from the collection chamber by holding the front panel away from the rear panel in the vicinity of the inlet port.

BRIEF DESCRIPTION OF THE DRAWINGS

FIG. 6 is a sectional view on an enlarged scale taken along line 6—6 of FIG. 1 with the bottom portion broken away;

FIG. 7 is a view similar to FIG. 6 but showing the urine meter in its vertical position.

Similar reference characters indicate similar parts throughout the several views of the drawings.

DESCRIPTION OF THE PREFERRED EMBODIMENT

Figure 1:
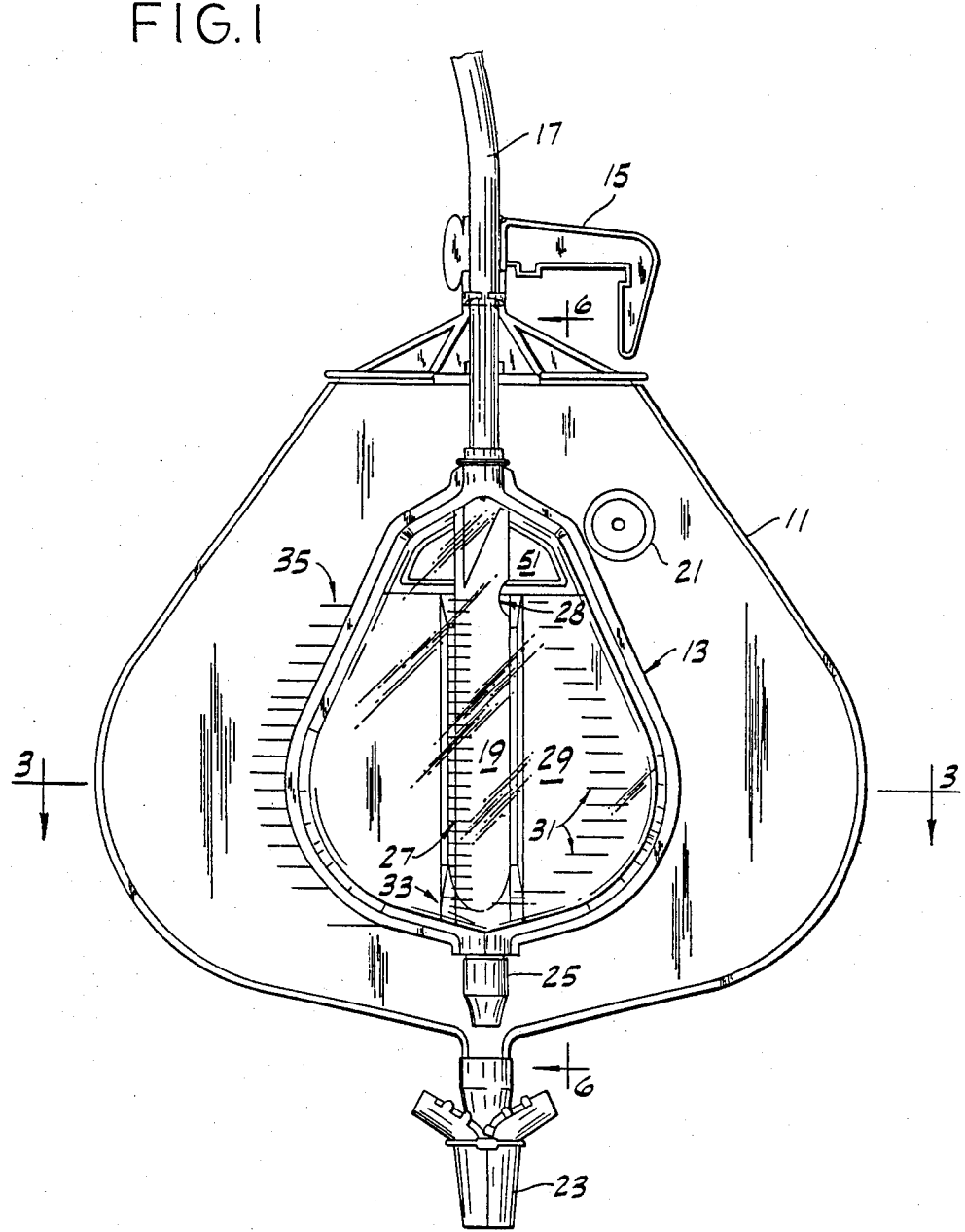
FIG. 1 is a front elevation of a urine meter and drainage bag combination of this invention.

Turning now to the drawings, there is shown in FIG. 1 a flexible urinary drainage bag 11 in combination with a relatively rigid urine metering collection chamber or urine meter 13. Bag 11 is suitably secured, by radio frequency sealing or the like, to a drainage bag support 15 such as is disclosed in co-assigned U.S. patent application Ser. No. 520,954 filed Aug. 5, 1983 so that in use bag 11 may be suspended vertically from a hospital bed or the like (not shown) to collect body fluids, e.g. urine, from a patient. Specifically, body fluid such as urine flows through a drain tube 17, which terminates at its distal end with an inclined cut, into a burette 19 disposed inside and constituting part of meter 13. Bag 11 also has a vent 21 of conventional design secured by radio frequency sealing or the like in the front thereof to permit the expulsion of air from bag 11 as the bag is filled with urine. At the lower end of the bag 11 is a manually actuable valve 23 which when open provides a path for urine to exit from the interior of bag 11. Meter 13 similarly has a manually operable valve 25 at its lower end for the same purpose.

Figure 8:
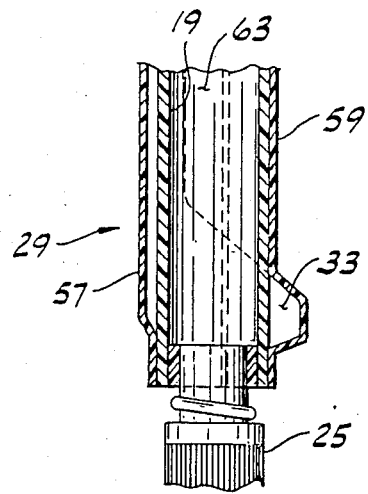
FIG. 8 is a sectional view taken along lines 8—8 of FIG. 4.

Burette 19 preferably is an extruded, relatively flexible tube of a plastic such as polyvinyl chloride (PVC). By way of example, burette 19 can have an outside diameter of about 0.75 inch (1.9 cm) and a wall of approximately 0.05 inch (1.5 mm). The burette extends from the bottom of meter 13 to generally the top thereof (approximately 6 inches (15.3 cm) for example) and is sealed at the bottom thereof to the body of the meter and valve 25 so that urine entering the burette from drain tube 17 fills burette 19 from the bottom without leaking out. Burette 19 can thus be used in conjunction with a set of gradations 27 printed or otherwise permanently affixed to the transparent vinyl (PVC) front of meter 13 to provide accurate measurement of a relatively small amount of urine, e.g. two to thirty ml. As urine fills the burette to or approaching the uppermost of gradations 27, it spills out of an opening 28 in burette 19 into the main body, labelled 29, of meter 13. Also printed or otherwise affixed on the face of meter 13 is a second set of gradations 31 which permit the measurement of somewhat larger amounts of urine, e.g. 35 to 200 ml, in the main body of the meter. As is best seen in FIG. 8, a passage 33 is provided in main body 29 behind burette 19 to ensure that urine levels in the main body of the meter on both sides of the burette are equal, so that the measurement given by gradations 31 is accurate.

For convenience, the front of bag 11 is also transparent or translucent, is preferably calendared, and has printed or otherwise affixed thereon a third set of gradations 35, so that the amount of urine in the bag itself, as opposed to in the meter, may be at least approximately measured in increments of, for example, from approximately 100 ml to approximately 1800 ml.

Figure 2:
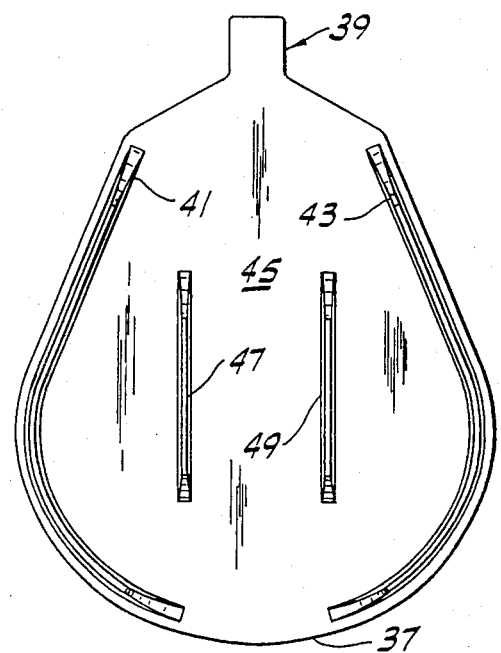
FIG. 2 is a front elevation of a spacer of this invention which is disposed in the combination of FIG. 1.
Figure 4:
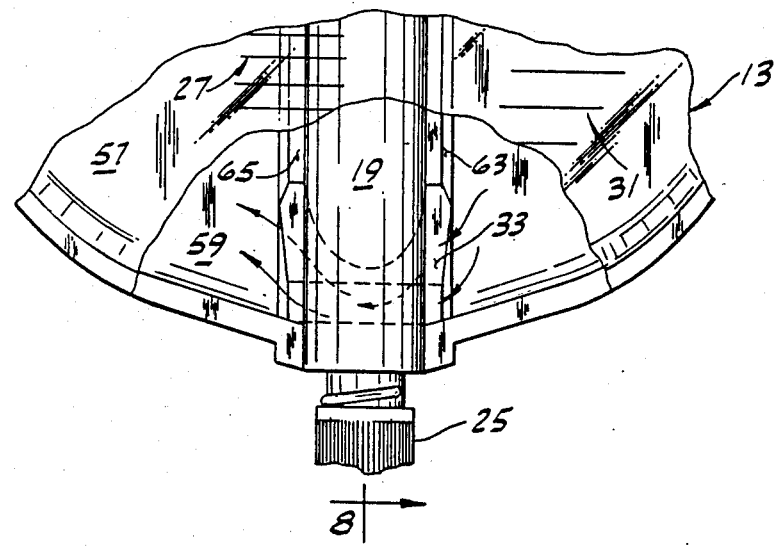
FIG. 4 is a front elevation, on an enlarged scale and with parts broken away, of the lower portion of the combination of FIG. 1.

A relatively planar spacer 37 (FIG. 2) of relatively rigid polyvinyl chloride material having a thickness of approximately 0.01 inch (0.25 mm) is provided for inclusion inside bag 11. At its top spacer 37 includes a tab 39 suitable for radio frequency sealing or the like to the top of bag 11 to hold spacer 37 in place inside the bag. Along its left and right peripheries, spacer 37 includes a pair of ribs 41, 43 which extend generally perpendicularly approximately 0.5 inch (12.5 mm) out from the main body, labelled 45, of spacer 37. The size and shape of spacer 37 and the placement of ribs 41 and 43 is selected so that the urine meter seats between ribs 41 and 43. Spacer 37 also includes a second pair of ribs 47, 49 extending generally perpendicularly approximately 0.3 inch (8 mm) out from main body 45, ribs 47 and 49 being generally paralled to the longitudinal axis of spacer 37. Ribs 47 and 49 are shorter in length than ribs 41 and 43 and, as best seen in FIG. 4, terminate at their upper end in the vicinity of an inlet port or opening 51 of bag 11.

Figure 3:
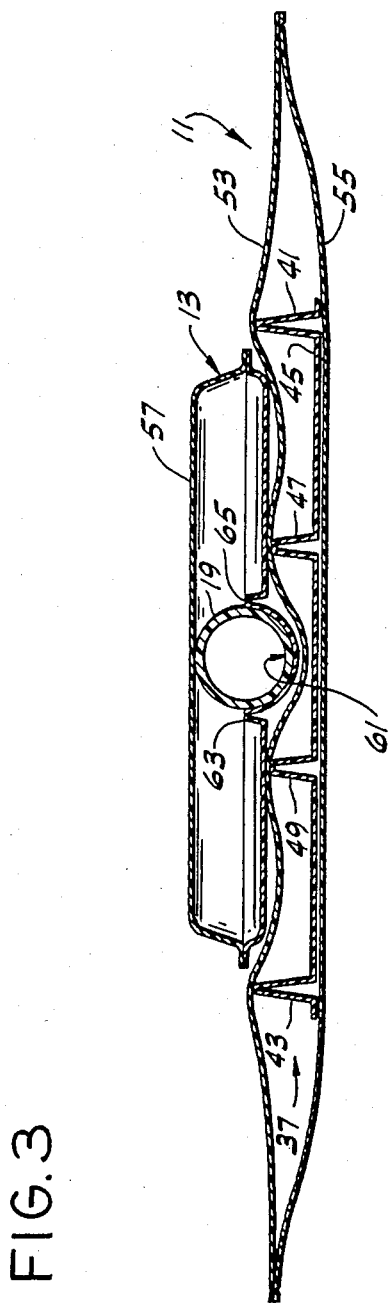
FIG. 3 is a sectional view on an enlarged scale taken along lines 3—3 of FIG. 1.

The lower portion of bag 11, meter 13, burette 19 and spacer 37 are shown in section in FIG. 3. Bag 11 is seen to have a relatively flexible, transparent front panel 53 of calendared vinyl (PVC) having a thickness of approximately 0.01 inch (0.25 mm) suitably secured as by radio frequency sealing at its periphery to a relatively flexible, opaque rear panel 55 of vinyl PVC of approximately the same thickness, said rear panel preferably being white to contrast with any urine in bag 11. Spacer 37 is disposed inside bag 11, i.e. between panels 53, 55 with ribs 41 and 43 being disposed exteriorly of meter 13. Ribs 47 and 49, on the other hand, can come into contact with the rear of meter 13 through front panel 53 of bag 11. Ribs 47 and 49 are not as tall (do not extend out from the body of spacer 37 as far) as ribs 41 and 43, thereby reducing the overall width of the bag and meter combination from what it would be if ribs 47 and 49 were as tall as ribs 41 and 43.

Meter 13 has a transparent, relatively rigid front panel 57 of vacuum formed polyvinyl chloride and an opaque, perferably white, rigid rear panel 59, also of vacuum formed polyvinyl chloride, which panels are suitably sealed together such as by radio frequency sealing along their edges, each panel having a thickness of approximately 0.025 inch (0.6 mm). Rear panel 59 has formed therein a recess or groove 61 and a pair of ribs 63, 65 to receive and support flexible burette tube 19 against transverse movement. The ribs also strengthen the meter itself and maintain the circular cross-section of the burette. Ribs 63 and 65 terminate short of the bottom of meter 13 (see FIG. 4) and channel 33 is formed in rear panel 59 (see FIG. 8) to permit urine to freely flow behind burette 19 to equalize the urine levels in each half of meter 13. Referring back to FIG. 3, front panel 57 supports burette 19 as well by being in frictional contact therewith even though the front panel is not molded to receive the burette.

Figure 5:
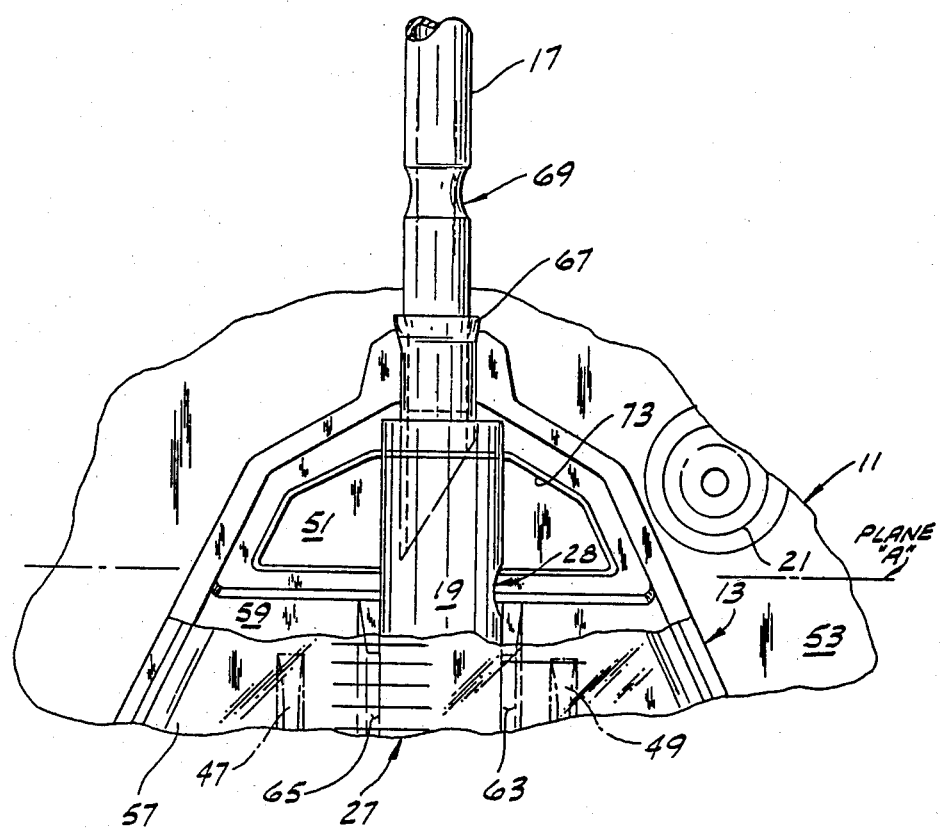
FIG. 5 is a front elevation, on an enlarged scale and with parts broken away, of the upper portion of the combination of FIG. 1.

The tops of meter 13 and burette 19 are shown in greater detail in FIG. 5. Drain tube 17 is secured in the top of meter 13 in a clear plastic bushing 67 of PVC whose inclined lower end terminates in burette 19 and which is itself secured by a suitable adhesive or sealing process to the top of meter 13. Rigid panels 57 and 59 extend around bushing 67 and help hold it in place. The inclined distal end of bushing 67 thus constitutes the inlet port of meter 13. Tube 17 generally from the inlet port of meter 13 upwardly a predetermined distance to a section thereof labelled 69 which has a length much shorter than the predetermined distance. At section 69 the wall of tube 17 has been thinned to provide a predetermined point of weakness. This thinning, which is exaggerated in FIGS. 5–7, is accomplished without changing the inner diamter of tube 17, which diameter remains substantially constant throughout its length by, for example, placing the distal portion of the tube over a mandrel and rotating it about its longitudinal axis while simultaneously heating section 69 and stretching the tube. By way of example, the inner diameter of tube 17 throughout its length is approximately 0.3 inch (8 mm) while the outer diameter can vary from 0.4 inch (1 cm) above and below section 69 to approximately 0.36 inch (9 mm) at section 69. However, even this much thinning of the wall is not necessary. All that is required is that the wall be thinned enough at section 69 to make section 69 the weakest part of the tube 17 so that when bent, the tube will kink off at that point.

The purpose of section 69 is illustrated in FIGS. 6 and 7. Rear panel 59 of urine meter 13 has an outlet port 71 molded therein with a lip 73 thereof which extends into and is suitably secured to front panel 53 of bag 11. As urine fills meter 13 to the bottom of outlet port 71, the urine spills over lip 73 through inlet port 51 of bag 11 into the bag. Many times, however, the meter is not allowed to become this full. Rather, periodically a nurse records the amount of urine in meter 13 and then rotates meter 13 from its generally vertical portion of FIG. 6 around plane A (FIG. 5) to a substantially horizontal position shown in FIG. 7 to dump the contents of the meter into the bag. Section 69, being the point of weakness, thereupon kinks off tube 17. This action closes the lumen of tube 17 and ensures that the urine passes into bag 11 instead of traveling up tube 17.

When the urine is dumped into bag 11, spacer 39 and specifically ribs 41, 43, 47 and 49 hold walls 53 and 55 of the bag apart to promote rapid dumping of the urine into the bag. The calendared texture of front panel 53 also promotes rapid dumping as it reduces the tending of the front and rear panels of the bag to stick together.

In view of the above it will be seen that the objects of the invention are achieved and other advantageous results attained.

Although the invention has been described with reference to the preferred embodiment illustrated in the drawings, many modifications will be apparent to those skilled in the art without departing from the spirit or scope of this invention.

What is claimed is:

1. In combination a drainage bag for body fluids such as urine, a spacer in said bag, and a rigid metering collection chamber, said bag having a flexible front panel constituting the front of the bag, a flexible rear panel constituting the rear of the bag, the flexible front and rear panels being secured together along their peripheries to form the bag, and an inlet port generally near to but spaced from the top of the bag to permit the flow of body fluids into the bag, said rigid metering collection chamber having an inlet port generally near the top thereof for connection to a drain tube or the like to receive body fluids from a patient to be measured, said chamber also having an outlet port generally near the top thereof in fluid communication with the inlet port of the drainage bag to permit body fluids from the metering collection chamber to be manually dumped therefrom into the drainage bag when the collection chamber is lifted from a generally vertical to a generally horizontal position, said spacer being positioned in the bag between the front and rear panels, said spacer having a relatively flat planar main body and at least two ribs extending generally perpendicularly out from the planar body and spaced from each other, said ribs extending at their upper ends to the vicinity of the inlet port of the bag to facilitate the entry of body fluids being dumped therein from the collection chamber by holding the front panel away from the rear panel in the vicinity of the inlet port, at least two ribs of the spacer following opposite portions of the contour of the rigid metering collection chamber, the spacing between the two ribs at any point measured perpendicularly to the longitudinal axis of the collection chamber being slightly greater than the width of the collection chamber at that point so that the collection chamber seats within the ribs of the spacer.

2. The combination as set forth in claim 1 wherein the spacer includes at least a third rib between the first two ribs, said third rib extending generally perpendicularly out from the main body of the spacer a shorter distance than the first two ribs so that the collection chamber is seated between the first two ribs and rests upon the third rib.

3. In combination a drainage collection bag for body fluids such as urine, a spacer means in said bag, and a rigid fluid metering chamber having front and rear panels, said bag having flexible front and rear panels secured together along their peripheries to form said bag, and an inlet port in said front panel generally near to but spaced from the top of the said bag to permit the flow of body fluids into said bag, said chamber having an inlet port generally near the top thereof for connection to a drain tube or the like to receive body fluids from a patient to be measured, said chamber also having an outlet port in said rear panel thereof generally near the top thereof, said rear panel of said chamber and said front panel of said bag being connected together with said outlet port connected in fluid communication with said bag inlet port and such that the lower end of said chamber is movable away from the lower end of said bag and body fluids from said chamber are flowable therefrom into said bag through said outlet port and said bag inlet port when said chamber is lifted from a generally vertical position toward a generally horizontal position, said spacer means being positioned between said front and rear panels and fixed to said bag at a point above said bag inlet port and extending downwardly across said bag inlet port to a point substantially below said bag inlet port for allowing said front panel to move away from said rear panel during movement of said chamber toward a horizontal position to facilitate fluid flow from said chamber through said bag inlet port into said bag.

4. The combination of claim 3 wherein said spacer means is formed of a plastic material which is less flexible than said front panel.

5. The combination of claim 4 wherein said spacer means includes at least a pair of spaced ribs extending from the spacer means in a direction toward said front panel.

6. The combination of claim 3 wherein said spacer means has a height and width greater than those of said bag inlet port.

7. The combination of claim 6 wherein said spacer means extends downwardly at least to the bottom of said chamber.

8. The combination of claim 6 wherein said spacer means has a height and width at least as great as those of said chamber.

9. The combination of claim 3 further including drain tube means connected to said chamber inlet port independently of said bag.

* * * * *